United States Patent
Bolin et al.

(10) Patent No.: US 8,039,495 B2
(45) Date of Patent: Oct. 18, 2011

(54) BIPHENYL CARBOXYLIC ACIDS AND BIOISOSTERES AS GLYCOGEN SYNTHASE ACTIVATORS

(75) Inventors: David Robert Bolin, Montclair, NJ (US); Yimin Qian, Wayne, NJ (US); Kshitij Chhabilbhai Thakkar, Clifton, NJ (US); Lin Yi, Basking Ridge, NJ (US); Weiya Yun, Warren, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 12/905,313

(22) Filed: Oct. 15, 2010

(65) Prior Publication Data
US 2011/0118322 A1 May 19, 2011

Related U.S. Application Data

(60) Provisional application No. 61/261,448, filed on Nov. 16, 2009.

(51) Int. Cl.
| | |
|---|---|
| A61K 31/426 | (2006.01) |
| A61K 31/40 | (2006.01) |
| A61K 31/198 | (2006.01) |
| A61K 31/18 | (2006.01) |
| A61K 31/41 | (2006.01) |
| C07D 207/16 | (2006.01) |
| C07D 403/04 | (2006.01) |
| C07D 277/56 | (2006.01) |
| C07C 235/42 | (2006.01) |
| C07C 311/51 | (2006.01) |
| A61P 3/10 | (2006.01) |
| A61P 3/00 | (2006.01) |

(52) U.S. Cl. ........ 514/365; 514/381; 514/423; 514/563; 514/605; 548/200; 548/253; 548/533; 562/444; 564/99

(58) Field of Classification Search ........................ None
See application file for complete search history.

(56) References Cited

FOREIGN PATENT DOCUMENTS

| | | |
|---|---|---|
| DE | 2842243 | 10/1980 |
| DE | 4142514 | 6/1993 |
| WO | 9740017 | 10/1997 |
| WO | 2004058679 | 7/2004 |
| WO | 2005000781 | 1/2005 |
| WO | 2007024922 | 3/2007 |
| WO | 2007044622 | 4/2007 |
| WO | 2008033455 | 3/2008 |

OTHER PUBLICATIONS

Stelmach et al., caplus an 2006:1005577.*
Brameld et al., caplus an 2010:115422.*
Pociecha et al., caplus an 2002:423496.*
Szydlowska et al., caplus an 1999:75052.*
Gunjima et al., caplus an 1987:431333.*

* cited by examiner

*Primary Examiner* — Sun Jae Loewe
(74) *Attorney, Agent, or Firm* — George W. Johnson; Dennis P. Tramaloni; Samuel H. Megerditchian

(57) ABSTRACT

Provided herein are compounds of the formula (I):

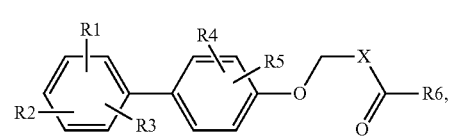

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

2 Claims, No Drawings

BIPHENYL CARBOXYLIC ACIDS AND BIOISOSTERES AS GLYCOGEN SYNTHASE ACTIVATORS

PRIORITY TO RELATED APPLICATION(S)

This application claims the benefit of U.S. Provisional Application No. 61/261,448, filed Nov. 16, 2009, which is hereby incorporated by reference in its entirety.

FIELD OF THE INVENTION

The invention is directed to compounds, salts and pharmaceutical compositions useful as activators of glycogen synthase for the treatment of metabolic diseases and disorders.

All documents cited or relied upon below are expressly incorporated herein by reference.

BACKGROUND OF THE INVENTION

Diabetes mellitus is a common and serious disorder, affecting 10 million people in the U.S. [Harris, M. I. Diabetes Care 1998 21 (3S) Supplement, 11C], putting them at increased risk of stroke, heart disease, kidney damage, blindness, and amputation. Diabetes is characterized by decreased insulin secretion and/or an impaired ability of peripheral tissues to respond to insulin, resulting in increased plasma glucose levels. The incidence of diabetes is increasing, and the increase has been associated with increasing obesity and a sedentary life. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. However, these factors are often unable to control the disease, and there are a number of drug treatments available, including insulin, metformin, sulfonylureas, acarbose, and thiazolidinediones. Each of these treatments has disadvantages and there is an ongoing need for new drugs to treat diabetes.

Metformin is an effective agent that reduces fasting plasma glucose levels and enhances the insulin sensitivity of peripheral tissue, mainly through an increase in glycogen synthesis [De Fronzo, R. A. Drugs 1999, 58 Suppl. 1, 29]. Metformin also leads to reductions in the levels of LDL cholesterol and triglycerides [Inzucchi, S. E. JAMA 2002, 287, 360]. However, it loses its effectiveness over a period of years [Turner, R. C. et al. JAMA 1999, 281, 2005].

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. Expert Opin. Investig. Drugs 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. JAMA 2002, 287, 360] and, like metformin, they lose efficacy over time [Turner, R. C. et al. JAMA 1999, 281, 2005]. A further problem often encountered in patients treated with sulfonylureas is hypoglycemia [Salas, M. and Caro, J. J. Adv. Drug React. Tox. Rev. 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. JAMA 2002, 287, 360].

Because none of these treatments is effective over the long term without serious side effects, there is a need for new drugs for the treatment of type 2 diabetes.

In skeletal muscle and liver, there are two major pathways of glucose utilization: glycolysis, or oxidative metabolism, where glucose is oxidized to pyruvate; and glycogenesis, or glucose storage, where glucose is stored in the polymeric form glycogen. The key step in the synthesis of glycogen is the addition of the glucose derivative UDP-glucose to the growing glycogen chain, and this step is catalyzed by the enzyme glycogen synthase [Cid, E. et al. J. Biol. Chem. 2000, 275, 33614]. There are two isoforms of glycogen synthase, found in liver [Bai, G. et al. J. Biol. Chem. 1990, 265, 7843] and in other peripheral tissues including muscle [Browner, M. F. et al. Proc. Nat. Acad. Sci. U.S.A. 1989, 86, 1443]. There is clinical and genetic evidence implicating both forms of glycogen synthase in metabolic diseases such as type 2 diabetes and cardiovascular disease. Both basal and insulin-stimulated glycogen synthase activity in muscle cells from diabetic subjects were significantly lower than in cells from lean non-diabetic subjects [Henry, R. R. et al. J. Clin. Invest. 1996, 98, 1231-1236; Nikoulina, S. E. et al. J. Clin. Enocrinol. Metab. 2001, 86, 4307-4314]. Furthermore, several studies have shown that levels of muscle [Eriksson, J. et al. N. Engl. J. Mod. 1989, 331, 337; Schulman, R. G. et al. N. Engl. J. Med. 1990, 332, 223; Thorburn, A. W. et al. J. Clin. Invest. 1991, 87, 489] and liver [Krssak, M. et. al. Diabetes 2004, 53, 3048] glycogen are lower in diabetic patients than in control subjects. In addition, genetic studies have shown associations in several populations between type 2 diabetes and/or cardiovascular disease and mutation/deletion in the GYS1 gene encoding the muscle isoform of glycogen synthase [Orhu-Melander, M. et al. Diabetes 1999, 48, 918; Fredriksson, J. et. al. PLoS ONE 2007, 3, e285; Kolhberg G. et. al. N. Engl. J. Med. 2007, 357, 1507]. Patients lacking GYS2 encoding the liver isoform of glycogen synthase, suffer from fasting ketotic hypoglycemia and postprandial hyperglycemia, hyperlactanemia and hyperlipidemia, supporting the essential role of liver GS in maintaining normal nutrient metabolism. [Weinstein, D. A. et. al. Mol. Genetics and Metabolism, 2006, 87, 284]

Glycogen synthase is subject to complex regulation, involving phosphorylation in at least nine sites [Lawrence, J. C., Jr. and Roach, P. J. Diabetes 1997, 46, 541]. The dephosphorylated form of the enzyme is active. Glycogen synthase is phosphorylated by a number of enzymes of which glycogen synthase kinase 3β (GSK3β) is the best understood [Tadayyon, M. and Smith, S. A. Expert Opin. Investig. Drugs 2003, 12, 307], and glycogen synthase is dephosphorylated by protein phosphatase type I (PP1) and protein phosphatase type 2A (PP2A). In addition, glycogen synthase is regulated by an endogenous ligand, glucose-6-phosphate which allosterically stimulates the activity of glycogen synthase by causing a change in the conformation of the enzyme that renders it more susceptible to dephosphorylation by the protein phosphatases to the active form of the enzyme [Gomis, R. R. et al. J. Biol. Chem. 2002, 277, 23246].

Several mechanisms have been proposed for the effect of insulin in reducing blood glucose levels, each resulting in an increase in the storage of glucose as glycogen. First, glucose uptake is increased through recruitment of the glucose transporter GLUT4 to the plasma membrane [Holman, G. D. and Kasuga, M. Diabetologia 1997, 40, 991]. Second, there is an increase in the concentration of glucose-6-phosphate, the allosteric activator of glycogen synthase [Villar-Palasi, C. and Guinovart, J. J. FASEB J. 1997, 11, 544]. Third, a kinase cascade beginning with the tyrosine kinase activity of the insulin receptor results in the phosphorylation and inactivation of GSK3β, thereby preventing the deactivation of glycogen synthase [Cohen, P. Biochem. Soc. Trans. 1993, 21, 555; Yeaman, S. J. Biochem. Soc. Trans. 2001, 29, 537].

Because a significant decrease in the activity of glycogen synthase has been found in diabetic patients, and because of its key role in glucose utilization, the activation of the enzyme glycogen synthase holds therapeutic promise for the treatment of metabolic diseases such as type 2 diabetes and cardiovascular diseases. The only known allosteric activators of the enzyme are glucose-6-phosphate [Leloir, L. F. et al. Arch. Biochem. Biophys. 1959, 81, 508] and glucosamine-6-phosphate [Virkamaki, A. and Yki-Jarvinen, H. Diabetes 1999, 48, 1101].

The following biaryloxymethylarenecarboxylic acids are reported to be commercially available from Otava, Toronto, Canada, Akos Consulting & Solutions, Steinen, Germany or Princeton BioMolecular Research, Monmouth Junction, N.J.: 4-(biphenyl-4-yloxymethyl)-benzoic acid, 3-(biphenyl-4-yloxymethyl)-benzoic acid, [4-(biphenyl-4-yloxymethyl)-phenyl]-acetic acid, [4-(4'-methyl-biphenyl-4-yloxymethyl)-phenyl]-acetic acid, 4-(4'-methyl-biphenyl-4-yloxymethyl)-benzoic acid, 3-(3-bromo-biphenyl-4-yloxymethyl)-benzoic acid, [4-(3-bromo-biphenyl-4-yloxymethyl)-phenyl]-acetic acid, 2-(4'-methyl-biphenyl-4-yloxymethyl)-benzoic acid, 5-(biphenyl-4-yloxymethyl)-furan-2-carboxylic acid, 5-(4'-methyl-biphenyl-4-yloxymethyl)-furan-2-carboxylic acid, 5-(3-bromo-biphenyl-4-yloxymethyl)-furan-2-carboxylic acid, 4-(biphenyl-4-yloxymethyl)-5-methyl-furan-2-carboxylic acid, 5-methyl-4-(4'-methyl-biphenyl-4-yloxymethyl)-furan-2-carboxylic acid, 4-(3-bromo-biphenyl-4-yloxymethyl)-5-methyl-furan-2-carboxylic acid, 2-(biphenyl-4-yloxymethyl)-4-methyl-thiazole-5-carboxylic acid, [2-(biphenyl-4-yloxymethyl)-thiazol-4-yl]-acetic acid, [2-(4'-methyl-biphenyl-4-yloxymethyl)-thiazol-4-yl]-acetic acid and [5-(biphenyl-4-yloxymethyl)-[1,3,4]oxadiazol-2-yl]-acetic acid.

Some biaryloxymethylarenecarboxylic acids are known in the art. However, none of these known compounds have been associated with either the treatment of diseases mediated by the activation of the glycogen synthase enzyme or to any pharmaceutical composition for the treatment of diseases mediated by the activation of the glycogen synthase enzyme. Andersen, H. S. et al. WO 9740017 discloses the structure and synthetic route to 3-(biphenyl-4-yloxymethyl)-benzoic acid as an intermediate in the synthesis of SH2 inhibitors. Winkelmann, E. et al. DE 2842243 discloses 5-(biphenyl-4-yloxymethyl)-thiophene-2-carboxylic acid as a hypolipemic agent. Mueller, T. et al. DE 4142514 discloses 2-(biphenyl-3-yloxymethyl)-benzoic acid as a fungicide. Ghosh, S. S. et al. WO 2004058679 discloses biaryloxymethylarene acids as ligands of adenine nucleoside translocase. Van Zandt, M. C. WO 2008033455 discloses biphenyl and heteroarylphenyl derivatives as protein phosphatase-1B inhibitors.

Glycogen synthase activators and stimulators of glycogen production have been reported. Chu, C. A et al. US 20040266856 discloses biaryoxymethylenecarboxylic acids as glycogen synthase activators. Chu, C. A. WO 2005000781 discloses biaryoxymethylarene carboxylic acids as activators of glycogen synthase. Yang, S-P. and Huang, Y. US 20050095219 discloses hyaluronic acid compounds that stimulate glycogen production. Gillespie, P. et al. WO 2005075468 discloses biaryoxymethylarene carboxylic acids as glycogen synthase activators. Gillespie, P. et al. WO 2006058648 discloses biaryoxymethylarene carboxylic acids as glycogen synthase activators. Bucala, R. et al. WO 2007044622 discloses macrophage migration inhibitory factor agonists that stimulate glycogen production.

SUMMARY OF THE INVENTION

The present invention is directed to compounds of the formula I:

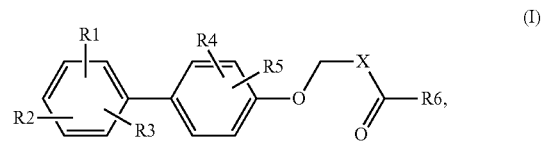

as well as pharmaceutically acceptable salts thereof, pharmaceutical compositions containing them and to methods of treating diseases and disorders. The compounds and compositions disclosed herein are glycogen synthase activators and are useful for the treatment of metabolic diseases and disorders, preferably diabetes mellitus, more preferably type II diabetes mellitus.

DETAILED DESCRIPTION OF THE INVENTION

In an embodiment of the present invention, provided is a compound of Formula (I):

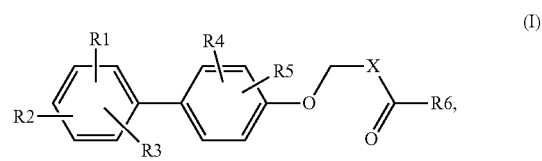

wherein:
X is phenyl or thiazole;
R1, R2, R3, independently of each other, is halogen, lower alkyl or alkoxy;
R4, R5, independently of each other, is halogen or hydrogen;
R6 is —NR7R8, unsubstituted pyrrolidine or pyrrolidine substituted with —COOH or tetrazole;
R7 is hydrogen or unsubstituted lower alkyl, branched or unbranched; and
R8 is —SO$_2$-lower alkyl, —SO$_2$-cycloalkyl, unsubstituted lower alkyl or lower alkyl mono- or bi-substituted independently with (=O), —NSO$_2$CH$_3$ or hydroxy,
or a pharmaceutically acceptable salt thereof.

Preferably, X is phenyl; R1, R2, R3, independently of each other, is halogen, lower alkyl or alkoxy; R4, R5, independently of each other, is halogen or hydrogen; R6 is —NR7R8, unsubstituted pyrrolidine or pyrrolidine substituted with —COOH or tetrazole; R7 is hydrogen or unsubstituted lower alkyl, branched or unbranched; and R8 is —SO$_2$-lower alkyl, —SO$_2$-cycloalkyl, unsubstituted lower alkyl or lower alkyl mono- or bi-substituted independently with (=O), —NSO$_2$CH$_3$ or hydroxy.

Preferably, X is thiazole; R1, R2, R3, independently of each other, is halogen, lower alkyl or alkoxy; R4, R5, independently of each other, is halogen or hydrogen; R6 is —NR7R8, unsubstituted pyrrolidine or pyrrolidine substituted with —COOH or tetrazole; R7 is hydrogen or unsubstituted lower alkyl, branched or unbranched; and R8 is —SO$_2$-lower alkyl, —SO$_2$-cycloalkyl, unsubstituted lower alkyl or lower alkyl mono- or bi-substituted independently with (=O), —NSO$_2$CH$_3$ or hydroxy.

Preferably, R1, R2, R3, independently of each other, is fluoro, chloro, methyl or methoxy.

Preferably, R4, R5, independently of each other, is hydrogen or fluoro.

Preferably, R1 is fluoro.
Preferably, R2 is fluoro.
Preferably, R3 is methyl or methoxy.
Preferably, R4 is hydrogen.
Preferably, R5 is fluoro.
Preferably, R6 is unsubstituted pyrrolidine.
Preferably, R6 is pyrrolidine substituted with —COOH or tetrazole.
Preferably, R6 is —NR7R8.
Preferably, R7 is methyl or tert-butyl.
Preferably, R7 is hydrogen.
Preferably, R8 is —CH$_2$COOH, —SO$_2$CH$_3$, —SO$_2$-cyclopropane or —CH$_2$C(O)NSO$_2$CH$_3$.

Preferably, said compound is:
(S)-1-[3-(2',4'-Difluoro-biphenyl-4-yloxymethyl)-benzoyl]-pyrrolidine-2-carboxylic acid;
(S)-1-[3-(4',5'-Difluoro-2'-methoxy-biphenyl-4-yloxymethyl)-benzoyl]-pyrrolidine-2-carboxylic acid;
(S)-1-[3-(4',5'-Difluoro-2'-methyl-biphenyl-4-yloxymethyl)-benzoyl]-pyrrolidine-2-carboxylic acid;
{[3-(4',5'-Difluoro-2'-methyl-biphenyl-4-yloxymethyl)-benzoyl]-methyl-amino}-acetic acid;
N-(2-Methanesulfonylamino-2-oxo-ethyl)-N-methyl-3-(2',4',5'-trifluoro-biphenyl-4-yloxymethyl)-benzamide;
[(S)-2-(1H-Tetrazol-5-yl)-pyrrolidin-1-yl]-[3-(2',4',5'-trifluoro-biphenyl-4-yloxymethyl)-phenyl]-methanone;
{[3-(4',5'-Difluoro-2'-methoxy-biphenyl-4-yloxymethyl)-benzoyl]-methyl-amino}-acetic acid;
{tert-Butyl-[3-(4',5'-difluoro-2'-methoxy-biphenyl-4-yloxymethyl)-benzoyl]-amino}-acetic acid;
{tert-Butyl-[2-(4',5'-difluoro-2'-methoxy-biphenyl-4-yloxymethyl)-thiazole-4-carbonyl]-amino}-acetic acid;
{Methyl-[3-(2',4',5'-trifluoro-biphenyl-4-yloxymethyl)-benzoyl]-amino}-acetic acid;
{Methyl-[3-(2,4',5'-trifluoro-2'-methoxy-biphenyl-4-yloxymethyl)-benzoyl]-amino}-acetic acid;
Cyclopropanesulfonic acid 3-(2',4',5'-trifluoro-biphenyl-4-yloxymethyl)-benzoylamide;
{[3-(4',5'-Difluoro-2'-methoxy-biphenyl-4-yloxymethyl)-4-fluoro-benzoyl]-methyl-amino}-acetic acid;
{{Methyl-[3-(3,2',4',5'-tetrafluoro-biphenyl-4-yloxymethyl)-benzoyl]-amino}-acetic acid; or
(R)-1-[3-(4',5'-Difluoro-2'-methoxy-biphenyl-4-yloxymethyl)-benzoyl]-pyrrolidine-2-carboxylic acid.

In another preferred embodiment, provided is a pharmaceutical composition, comprising a therapeutically effective amount of a compound according to formula (I) and a pharmaceutically acceptable carrier and/or adjuvant.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, indenyl and the like. In a preferred embodiment, the "cycloalkyl" moieties can optionally be substituted with one, two, three or four substituents with the understanding that said substituents are not, in turn, substituted further unless indicated otherwise in the Examples or claims below. Each substituent can independently be, for example, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, pyranyl, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below. Substituents may include, for example, —COOH and a heteroaryl group, such as, for example, tetrazole.

The term "lower alkyl", alone or in combination with other groups, refers to a branched or straight-chain alkyl radical of one to nine carbon atoms, preferably one to six carbon atoms, most preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl and naphthyl.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. Substituents may include, for example, (=O), —NSO$_2$CH$_3$ and hydroxy groups.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. The heteroaryl group may be substituted independently with one, two, or three substituents, with the understanding that said substituents are not, in turn, substituted further unless indicated otherwise in the Examples or claims below. Substituents may include, for example, halogen and lower alkyl groups.

As used herein, the term "alkoxy" means alkyl-O—; and "alkoyl" means alkyl-CO—. Alkoxy substituent groups or alkoxy-containing substituent groups may be substituted by, for example, one or more alkyl groups with the understanding that said substituents are not, in turn, substituted further unless indicated otherwise in the Examples or claims below.

As used herein, the term "halogen" means fluorine, chlorine, bromine or iodine radical, preferably fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminium salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula (I) in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Outlined below are reaction schemes suitable for preparing such compounds. Further exemplification can be found in the specific Examples detailed below.

Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

DEFINITIONS AS USED HEREIN INCLUDE

GS is glycogen synthase,
THF is tetrahydrofuran,
DMF is N,N-dimethylformamide,
DMA is N,N-dimethylacetamide,
DMSO is dimethylsulfoxide,
DCM is dichloromethane,
DME is dimethoxyethane,
MeOH is methanol,
EtOH is ethanol,
NaOH is sodium hydroxide,
TFA is 1,1,1-trifluoroacetic acid, HOBT is 1-hydroxybenzotriazole,
PyBroP is bromotripyrrolidinophosphonium hexafluorophosphate,
EDCI is 1-[3-(dimethylamino)propyl]-3-ethylcarbodiimide hydrochloride,
DIPEA is diisopropylethylamine,
Boc is tert-butyloxycarbonyl,
NBS is N-bromosuccinimde,
Q-Phos is 1,2,3,4,5-pentaphenyl-1'-(di-tert-butylphosphino)ferrocene,
EDCI is N-(3-dimethylaminopropyl)-N'-ethylcarbodiimide,
HOAT is 1-hydroxy-7-azabenzotriazole,
DBU is 1,8-diazabicyclo[5,4,0]undec-7-ene,
CDI is 1,1'-carbonyldiimidazole,
Brine is saturated aqueous sodium chloride solution,
TLC is thin layer chromatography,
RP HPLC is reversed phase high performance liquid chromatography,
HR-MS is high resolution mass spectrometry,
LC-MS is liquid chromatographic mass spectrometry,
RT is room or ambient temperature.

The preparation of substituted biphenylphenols is described in Scheme 1, below. Commercially available phenylboronic acid (i) can be coupled with 4-halo-phenol (ii) under palladium catalysis conditions to form the bi-aryl-phenol (iii), where R1, R2 and R3 can be fluoro, chloro, methyl or methoxy groups, R4 and R5 may be H or fluoro and halo may be iodo or bromo. Alternatively, the required biphenylphenol (iii) can also be prepared through the coupling of 4-hydroxy-arylboronic acid with the corresponding arylbromide (iv) under palladium catalysis conditions (Scheme 1). Non-commercially available aryl-boronate esters (v) may be prepared from the corresponding halogen derivatives vii, where halo may be iodo or bromo. Non-commercially available arylbromides (iv) can be prepared through aromatic bromination of vi.

The preparation of substituted aryl-carboxylic acids (xi) is shown in Scheme 2. Bromomethyl-aryl esters (viii), where R6 is lower alkyl, preferably methyl or ethyl, can be treated with substituted-biaryphenols under basic conditions, such as potassium carbonate, to give ester (x). Esters such as (x) may be hydrolyzed under basic conditions, such as lithium or sodium hydroxide, to give aryl acids, (xi), where R1, R2 and R3 can be fluoro, chloro, methyl or methoxy groups, R4 and R5 may be H or fluoro.

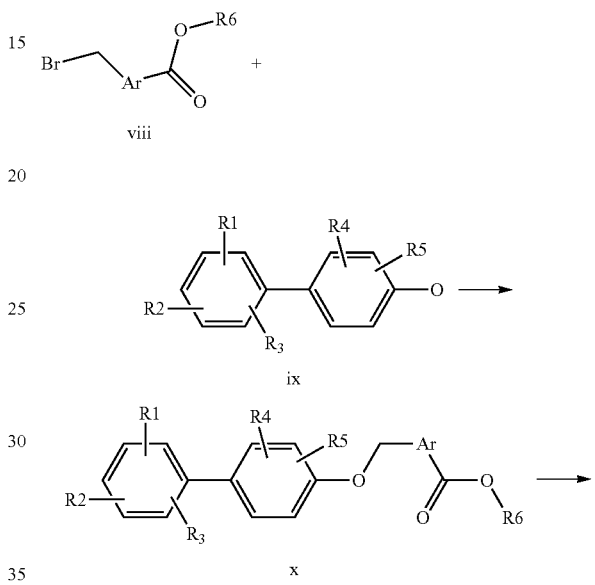

Scheme 2

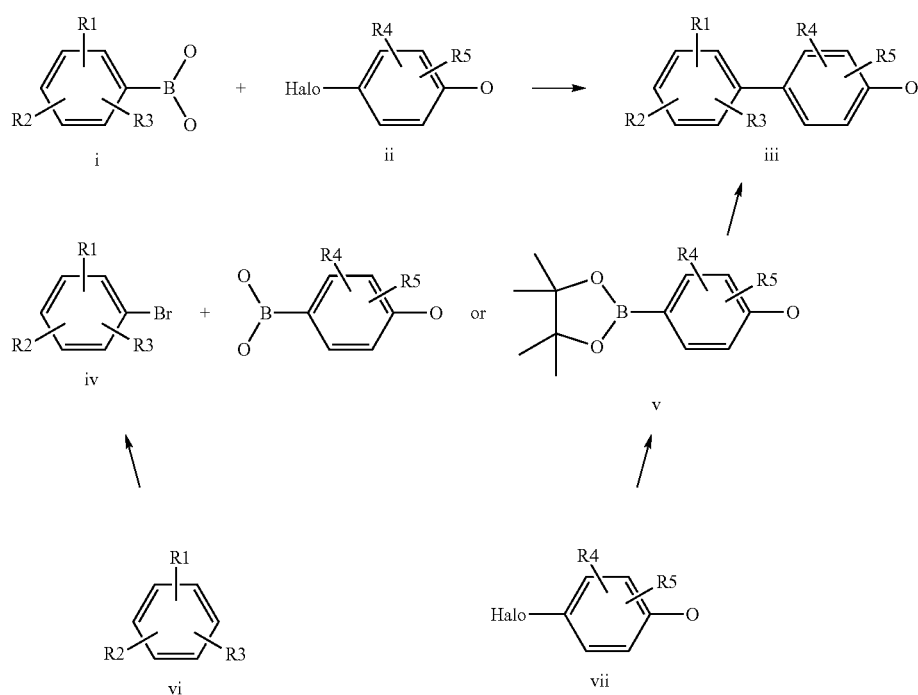

Scheme 1

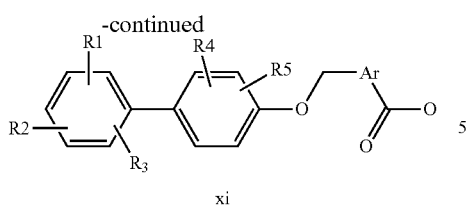

Substituted bromomethyl-aryl esters (xiv) may be prepared as shown in Scheme 3. 4-Fluoro-3-methyl-benzoic acid (xii) can be esterified under acidic conditions to give ester (xiii), where R6 is lower alkyl, preferably methyl or ethyl. Compound (xiii) may be brominated with N-bromo-succinimide in CCl4 in the presence of a radical initiator, such as 2,2'-azobis(2-methylpropionitrile) to give bromomethyl-aryl ester, (xiv).

Scheme 3

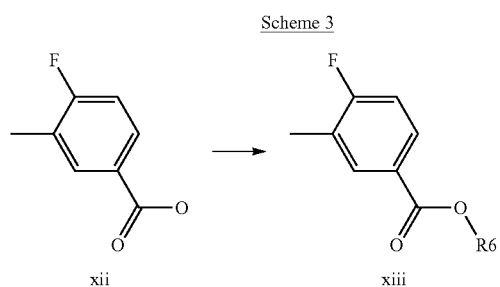

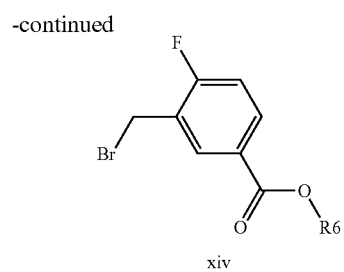

Bromomethyl-aryl esters (viii) may be reacted, as shown is Scheme 4, with substituted-phenols (ii), where R4 and R5 may be H or fluoro, under basic conditions to give ether (xv). Ether (xv) can be coupled with boronic acid (i) under palladium catalysis conditions to form the bi-aryl-ether (xviii), where R1, R2 and R3 can be fluoro, chloro, methyl or methoxy groups, R4 and R5 may be H or fluoro. Alternatively, ether (xv) may be treated with a bis(pinacolato)diboron to form the pinacolate (xvi), which may be coupled with arylhalide (xvii) under palladium catalysis conditions to form the bi-aryl-ether (xviii), where R1, R2 and R3 can be fluoro, chloro, methyl or methoxy groups, R4 and R5 may be H or fluoro. The esters (xviii) may be hydrolyzed under basic conditions, such as lithium or sodium hydroxide, to give aryl acids, (xix), where R1, R2 and R3 can be fluoro, chloro, methyl or methoxy groups, R4 and R5 may be H or fluoro.

Scheme 4

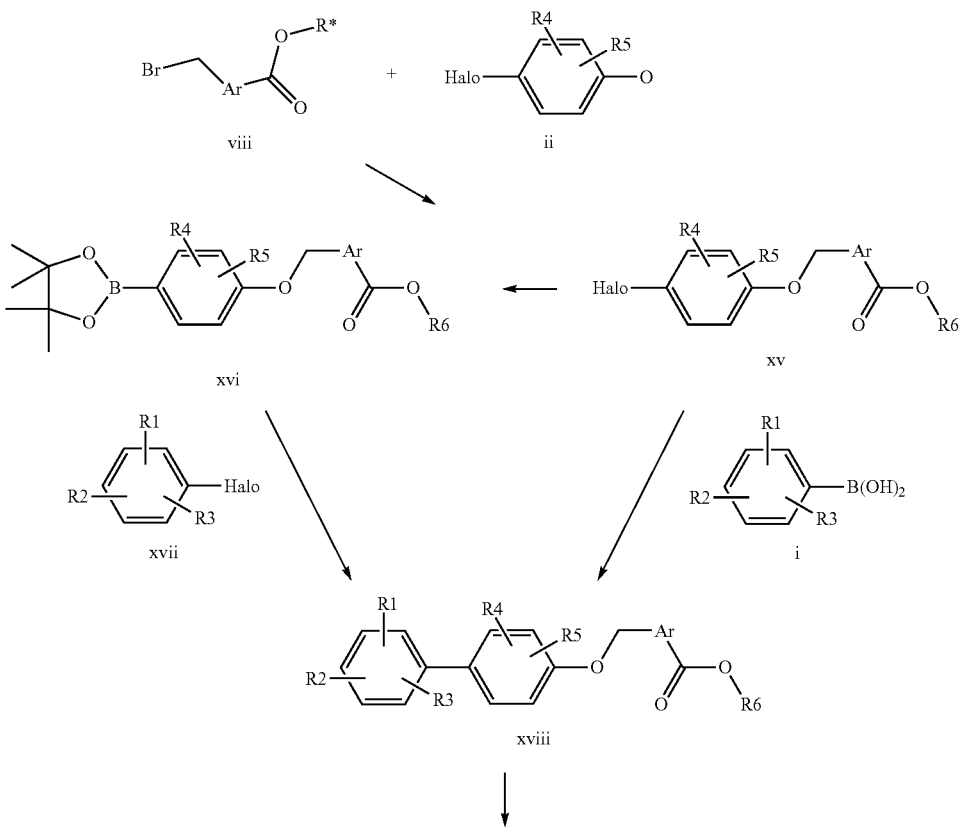

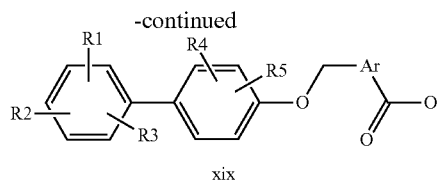

Acids xx may be prepared as shown in Scheme 5. Aryl acid xix may be first treated with thionyl chloride, to form an intermediate acid chloride, that may then be treated with a secondary amino acid, either cyclic or acylic, under basic conditions to give acid (xx). In the case of acylic amino acids, M may be lower alkyl, preferably methyl or tert-butyl. Alternatively, acid (xix) may be coupled with an amino acid ester under standard conditions such as EDCI to give ester (xxi), which may be hydrolyzed under basic conditions, such as lithium or sodium hydroxide, to give aryl acids, xx, where R1, R2 and R3 can be fluoro, chloro, methyl or methoxy groups, R4 and R5 may be H or fluoro.

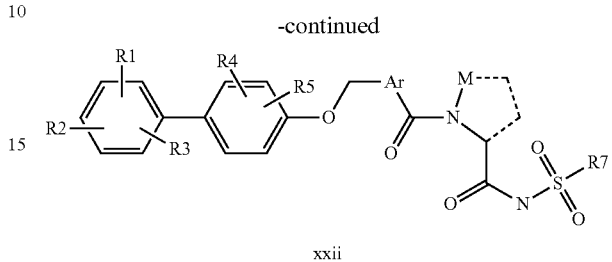

Scheme 5

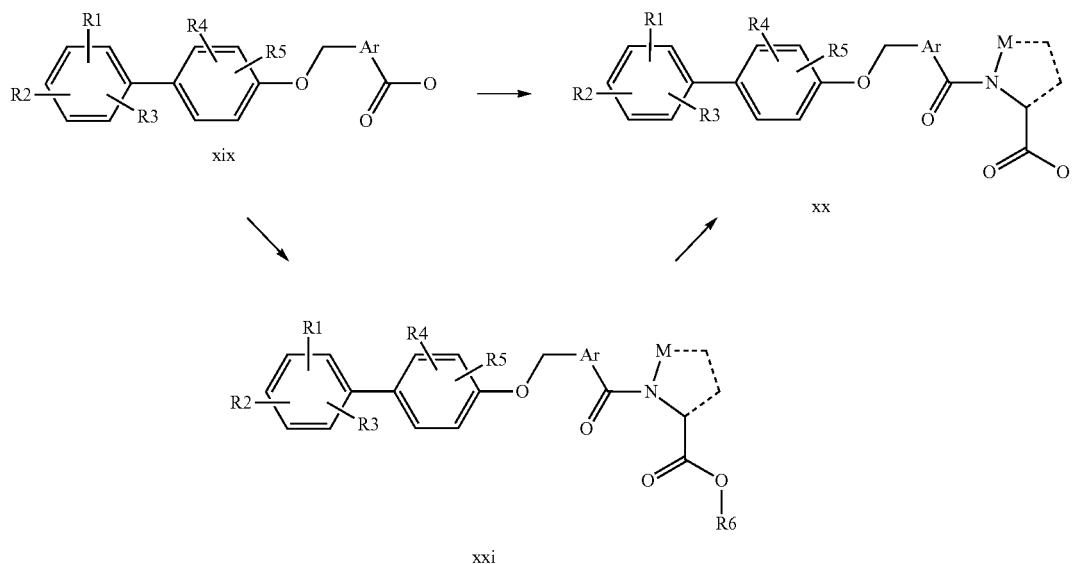

N-acyl-sulfonamides may be prepared as shown in Scheme 6. Acids (xx) may be treated with an alkyl sulfonamide under standard coupling conditions, preferably CDI with DBU, to give acyl-sulfonamide (xxii), where R1, R2 and R3 can be fluoro, chloro, methyl or methoxy groups, R4 and R5 may be H or fluoro and R7 is lower alkyl, preferably methyl or cyclopropyl.

Tetrazole xxiv may be prepared from aryl acid (xix) as shown in Scheme 7. Intermediate nitrile (xxiii) may be prepared under standard coupling conditions, such as through the acid chloride. Tetrazole (xxiv) may be prepared by heating nitrile (xxiii) with sodium azide and triethylammonium hydrochloride, where R1, R2 and R3 can be fluoro, chloro, methyl or methoxy groups, R4 and R5 may be H or fluoro.

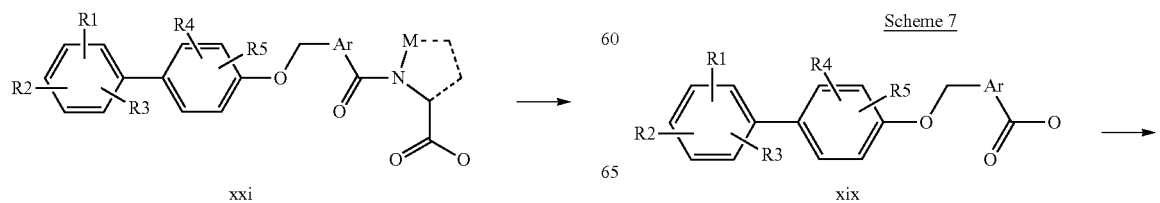

-continued

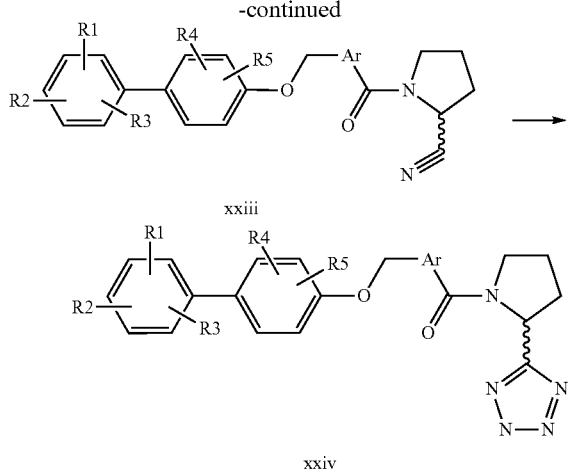

The invention will now be further described in the Examples below, which are intended as an illustration only and do not limit the scope of the invention.

EXAMPLES

Part I: Preparation of Preferred Intermediates 3-(4-Iodo-phenoxymethyl)-benzoic acid methyl ester

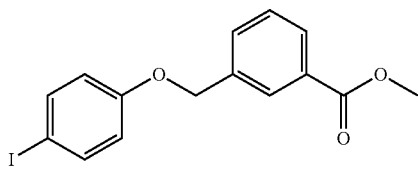

Methyl 3-bromomethyl benzoate (11.45 g, 50 mmol), 4-iodophenol (11.77 g, 53.5 mmol), and dried, finely ground potassium carbonate (7.39 g, 53.5 mmol) in 500 mL acetone were refluxed under argon for 20 hrs. The reaction mixture was cooled, concentrated and dissolved in 150 mL ethyl acetate. The ethyl acetate solution was washed with 150 mL H₂O, saturated NaHCO₃, saturated NaCl, dried over MgSO₄, filtered and evaporated in vacuo to an oil. The crude product was recrystallized from ethyl acetate hexanes to yield 12.6 g (68.4%) of 3-(4-iodo-phenoxymethyl)-benzoic acid methyl ester as a solid.

3-(2',4'-Difluoro-biphenyl-4-yloxymethyl)-benzoic acid

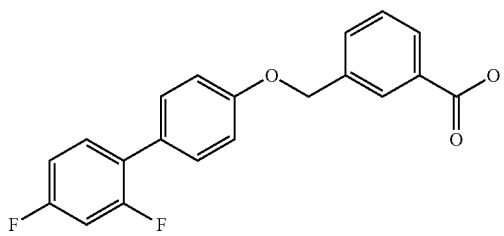

Bis(tricyclohexylphosphine)palladium (250 mg, 0.375 mmol) was added to a stirred solution of 3-(4-iodo-phenoxymethyl)-benzoic acid methyl ester (4.6 g, 12.5 mmol) and 2,4-difluorophenylboronic acid (3.92 g, 25 mmol) in 125 mL dioxane. Argon was bubbled through the solution for 5 min. H₂O (12.5 mL) was then added followed by dried, powdered potassium carbonate (3.45 g, 25 mmol). The mixture was heated to 100-105° C. under argon for 1 hr, cooled and distributed between 100 mL ethyl acetate and 100 mL H₂O. The ethyl acetate layer was washed with saturated NaCl, dried over MgSO₄ and concentrated in vacuo. The crude product was purified by flash chromatography with a gradient of 0-5% ethyl acetate in hexanes to yield 4.2 g of 3-(2',4'-difluoro-biphenyl-4-yloxymethyl)-benzoic acid methyl ester.

3-(2',4'-Difluoro-biphenyl-4-yloxymethyl)-benzoic acid methyl ester (4.2 g, 11.86 mmol) and 2N KOH (23.72 mL, 47.45 mmol) in 210 mL MeOH were refluxed for 1 hr. The reaction mixture was cooled, concentrated and distributed into 200 mL H₂O and 200 mL ethyl acetate. The aqueous layer was acidified with 2N HCl and separated. The organic layer was washed with saturated NaCl, dried over MgSO₄, filtered and concentrated in vacuo to yield 4.0 g (99.1%) of 3-(2',4'-difluoro-biphenyl-4-yloxymethyl)-benzoic acid as a white powder. LC-MS (ES) calculated for C20H14F2O3, 340.33; found m/z 339.1 [M−H]⁻.

3-(4',5'-Difluoro-2'-methoxy-biphenyl-4-yloxymethyl)-benzoic acid

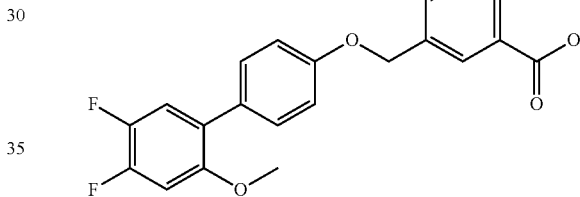

Bis(tricyclohexylphosphine)palladium (236 mg, 0.35 mmol) was added to a stirred solution of 3-(4-iodo-phenoxymethyl)-benzoic acid methyl ester (6.5 g, 17.73 mmol), potassium carbonate (3.67 g, 26.6 mmol) and 4,5-difluoro-2-methoxyphenylboronic acid (5 g, 26.6 mmol) in 156 ml, dioxane were reacted as above and purified by flash chromatography with a gradient of 0-5% ethyl acetate in hexanes to give 6.51 g (95.6%) of 3-(4',5'-difluoro-2'-methoxy-biphenyl-4-yloxymethyl)-benzoic acid methyl ester.

3-(4',5'-Difluoro-2'-methoxy-biphenyl-4-yloxymethyl)-benzoic acid methyl ester (6.5 g, 16.92 mmol) and 2N KOH (33.84 mL, 67.68 mmol) in 100 mL MeOH were reacted as above to yield 6.1 g (97.4) of 3-(4',5'-difluoro-2'-methoxy-biphenyl-4-yloxymethyl)-benzoic acid. LC-MS (ES) calculated for C21H16F2O4, 370.36; found m/z 369 [M−H]⁻.

3-(4',5'-Difluoro-2'-methyl-biphenyl-4-yloxymethyl)-benzoic acid

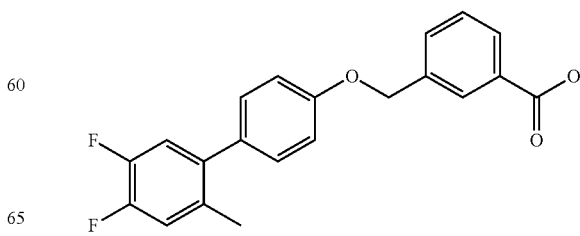

3-(4-Iodo-phenoxymethyl)-benzoic acid methyl ester (2.5 g, 6.79 mmol), bis(pinacolato)diboron (3.2 g, 13.58 mmol) and potassium acetate (3.3 g, 33.95 mmol) in 50 mL DMF with argon bubbling through the solution for 5 min. Bis(tricyclohexylphosphine)palladium (250 mg, 0.375 mmol) was added and the mixture was heated to 90° C. under argon for 2 hrs. The reaction mixture was cooled, diluted with 50 mL ethyl acetate, washed with $H_2O$, saturated NaCl, dried over $Na_2SO4$ and concentrated in vacuo. The crude product was purified by flash chromatography with a gradient of 0-7% ethyl acetate in hexanes to yield 1.68 g (67%) of 3-(4-(4',4',5',5'-tetramethyl-1',3',2'-dioxaborolan-2-yl)phenoxymethyl)-benzoic acid methyl ester. LC-MS (ES) calculated for $C_{21}H_{16}F_2O_3$, 354.36; found m/z 355 [M+H]$^+$.

Bis(tricyclohexylphosphine)palladium (91 mg, 0.136 mmol) was added to a stirred solution of 3-(4-(4',4',5',5'-tetramethyl-1',3',2'-dioxaborolan-2-yl)phenoxymethyl)-benzoic acid methyl ester (1.68 g, 4.565 mmol), 1M potassium carbonate (5.7 mL, 5.7 mmol) and 1-bromo-4,5-difluoro-2-methyl-benzene (0.945 g, 4.565 mmol) in 50 mL dioxane and 5 mL $H_2O$ were reacted as above and purified by flash chromatography with a gradient of 0-5% ethyl acetate in hexanes to give 1.33 g (79.2%) of 3-(4',5'-difluoro-2'-methyl-biphenyl-4-yloxymethyl)-benzoic acid methyl ester. LC-MS (ES) calculated for $C_{21}H_{16}F_2O_3$, 354.36; found m/z 353 [M-H]$^-$.

3-(4',5'-Difluoro-2'-methyl-biphenyl-4-yloxymethyl)-benzoic acid methyl ester (1.33 g, 3.61 mmol) and 2N KOH (7.23 mL, 14.45 mmol) in 21 mL MeOH and 7 mL $H_2O$ were reacted as above to yield 1.185 g (92.7%) of 3-(4',5'-difluoro-2'-methoxy-biphenyl-4-yloxymethyl)-benzoic acid. LC-MS (ES) calculated for $C_{21}H_{16}F_2O_3$, 354.36; found m/z 353 [M-H]$^-$.

3-(2',4',5'-Trifluoro-biphenyl-4-yloxymethyl)-benzoic acid

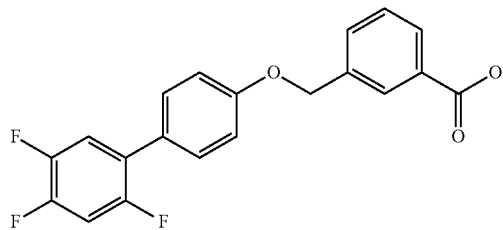

Bis(tricyclohexylphosphine)palladium (200 mg, 0.3 mmol) was added to a stirred solution of 3-(4-iodo-phenoxymethyl)-benzoic acid methyl ester (3.68 g, 10 mmol), potassium carbonate (2.76 g, 20 mmol) and 2,4,5-trifluorophenylboronic acid (3.5 g, 20 mmol) in 100 mL dioxane and 10 mL $H_2O$ were reacted as above and purified by flash chromatography with a gradient of 0-5% ethyl acetate in hexanes to give 2.9 g (77.9%) of 3-(2',4',5'-trifluoro-biphenyl-4-yloxymethyl)-benzoic acid methyl ester.

3-(2',4',5'-Trifluoro-biphenyl-4-yloxymethyl)-benzoic acid methyl ester (2.9 g, 7.79 mmol) and 2N KOH (15.6 mL, 31.2 mmol) in 140 mL MeOH were reacted as above to yield 2.6 g (93.2%) of 3-(2',4',5'-trifluoro-biphenyl-4-yloxymethyl)-benzoic acid. LC-MS (ES) calculated for $C_{20}H_{13}F_3O_3$, 358.32; found m/z 357.1 [M-H]$^-$.

3-(4',5'-Difluoro-2'-methoxy-biphenyl-4-yloxymethyl)-4-fluoro-benzoic acid

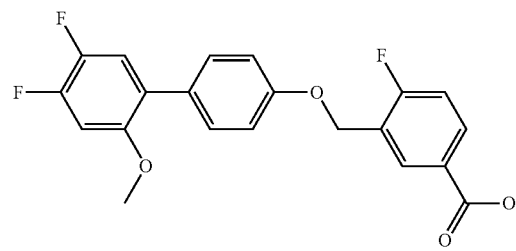

To a solution of 4-fluoro-3-methylbenzoic acid (5.0 g, 32.4 mmol) in methanol (150 mL) was added concentrated hydrochloric acid (2 mL). The mixture was refluxed for 4 hrs and then concentrated. The residue was treated with ether (200 mL) and washed with water, 10% sodium hydroxide solution, water and finally brine. The organic layer was dried over sodium sulfate and solvents were removed to give 4-fluoro-3-methylbenzoic acid methyl ester (4.56 g, 83.7%) as an off-white solid.

4-Fluoro-3-methylbenzoic acid methyl ester (4.56 g, 2.71 mmol) was suspended in carbon tetrachloride (80 mL) and benzoyl peroxide (1.0 g, 75% by weight, 3.0 mmol) was added. The mixture was refluxed for 6 hrs and the solid was filtered. The filtrate was concentrated and purified through flash column chromatography (200 g silica gel, 0% to 15% ethyl acetate in hexanes over 50 minutes) to give 3-bromomethyl-4-fluorobenzoic acid methyl ester as a white solid (3.0 g, 45%).

3-Bromomethyl-4-fluorobenzoic acid methyl ester (3.0 g, 12.1 mmol) was mixed with 4-iodophenol (3.2 g, 14.6 mmol) in acetone (75 mL) containing dry potassium carbonate (2.5 g, 18 mmol). The mixture was refluxed for 6 hrs and then filtered. The filtrate was concentrated and extracted with ether and water. The organic layer was dried over sodium sulfate and solvents were evaporated. The residue was purified through flash column chromatography (120 g silica gel, 0% to 20% ethyl acetate in hexanes over 40 minutes) to give clear oil as 4-fluoro-3-(4-iodophenoxy)methylbenzoic acid methyl ester (3.48 g, 74.4%).

To a mixture of 4-fluoro-3-(4-iodophenoxy)methylbenzoic acid methyl ester (1.1 g, 2.85 mmol) and 4,5-difluoro-2-methoxyphenylboronic acid (0.642 g, 3.4 mmol) in DMF (15 mL) and water (2.5 mL) was added Pd(dppf)Cl$_2$ (220 mg, 0.27 mmol) and potassium carbonate (1.24 g, 9.0 mmol). The mixture was stirred at 45° C. overnight and solvents were evaporated. The residue was extracted with ethyl acetate and water. The organic layer was dried and concentrated. The residue was purified through flash column chromatography (120 g silica gel, 5% to 40% ethyl acetate in hexanes over 25 minutes) to give a white solid as 3-(4',5'-difluoro-2'-methoxy-biphenyl-4-yloxymethyl)-4-fluorobenzoic acid methyl ester (0.76 g, 67%).

3-(4',5'-Difluoro-2'-methoxybiphenyl-4-yloxymethyl)-4-fluorobenzoic acid methyl ester (0.76 g, 1.9 mmol) was dissolved in THF (10 mL) and lithium hydroxide solution (0.5N, 8 mL) was added followed by addition of methanol (2 mL). The mixture was refluxed for 2 hrs and solvents were evaporated. The mixture was extracted with ether and water. The aqueous layer was treated with hydrochloric acid (1N, 5 mL) and extracted with ethyl acetate. The organic layer was washed with brine and dried over sodium sulfate. Solvents were evaporated to give a white solid as 3-(4',5'-difluoro-2'-methoxybiphenyl-4-yloxymethyl)-4-fluorobenzoic acid (0.7 g, 96%). HRMS-ES calculated for $C_{21}$, $H_{15}$, $F_3$, $O_4$, 411.0814; found m/z 411.0815 [M+Na]$^+$; $^1$H-NMR (DMSO-$d_6$) δ ppm 13.15 (br, s, 1H), 8.16 (dd, J=7.2, 1.8 Hz, 1H), 7.96-8.04 (m, 1H), 7.32-7.45 (m, 4H), 7.24 (dd, J=13.0, 6.9 Hz, 1H), 7.08 (d, J=8.5 Hz, 2H), 5.24 (s, 2H), 3.76 (s, 3H).

4',5'-Difluoro-2'-methoxy-biphenyl-4-ol

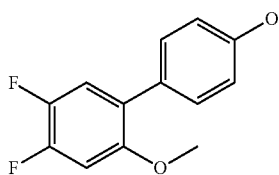

4,5-Difluoro-2-methoxyphenyl-boronic acid (8.8 g, 46.82 mmol) and 4-iodophenol (6.86 g, 31.21 mmol) were suspended in 165 ml of DMF. H2O (40 mL) was added and the mixture was degassed with argon. Finely ground potassium carbonate (13 g, 93.63 mmol) and tetrakis(triphenylphosphine) palladium(0) (1.5 g, 1.29 mmol) were added. The reaction was stirred at 80-85° C. for 1 hr under argon and cooled. The mixture was diluted with ethyl acetate and water. The organic layer was washed with brine, dried and solvents were evaporated. The crude product was purified by flash chromatography, eluting with 0-8% ethyl acetate in hexanes to yield 4',5'-difluoro-2'-methoxy-biphenyl-4-ol (6.58 g, 89.3%). LR-MS (ES) calculated for C13H10F2O2, 236.22; found m/z 235 [M–H]$^-$.

2-(4',5'-difluoro-2'-methoxy-biphenyl-4-yloxymethyl)-thiazole-4-carboxylic acid

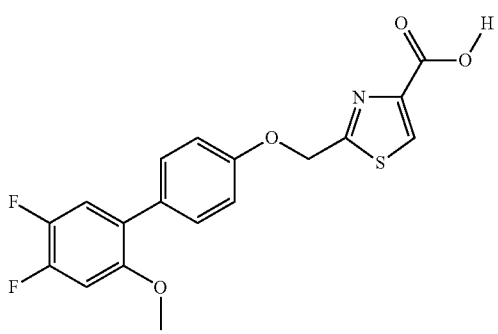

A mixture of 2-bromomethyl-thiazole-4-carboxylic acid ethyl ester (prepared according to US 2004/0266856 A1) (3.0 g, 11.99 mmol), 4',5'-difluoro-2'-methoxy-biphenyl-4-ol (3.09 g, 13.08 mmol), potassium carbonate (6.5 g, 47.03 mmol) and potassium iodide (1.1 g, 6.626 mmol) in DMF (25 mL) was heated under microwave conditions at 130° C. for 15 min. The reaction mixture was diluted with water (150 mL) and extracted with ethyl acetate (3×150 mL). The organic layers were combined, washed with 1/1 water/brine (2×100 mL) and brine (100 mL), dried (MgSO$_4$), filtered, concentrated and purified by flash chromatography (silica, 120 g, 20% to 100% ethyl acetate in hexanes) to give 2-(4',5'-difluoro-2'-methoxy-biphenyl-4-yloxymethyl)-thiazole-4-carboxylic acid ethyl ester (4.35 g, 89.5%) as an orange oil. LC-MS (ES) calculated for $C_{20}H_{17}F_2NO_4S$, 405.42; found m/z 406 [M+H]$^+$.

A solution of 2-(4',5'-difluoro-2'-methoxy-biphenyl-4-yloxymethyl)-thiazole-4-carboxylic acid ethyl ester (2.38 g, 5.870 mmol) in THF (40 mL) was treated with a solution of lithium hydroxide monohydrate (2.6 g, 61.96 mmol) in water (40 mL) at room temperature and stirred at 60° C. for 2 h. The mixture was cooled, diluted with water (75 mL), acidified with aq. 3N HCl and extracted with ethyl acetate (3×100 mL). The organic layers were combined, washed with brine (100 mL), dried (MgSO$_4$), filtered and concentrated to 2-(4',5'-difluoro-2'-methoxy-biphenyl-4-yloxymethyl)-thiazole-4-carboxylic acid (2.13 g, 96.1%) as a pale yellow solid. LC-MS (ES) calculated for $C_{18}H_{13}F_2NO_4S$, 377.37; found m/z 378 [M+H]$^+$.

3-(4-Bromo-3-fluoro-phenoxymethyl)-benzoic acid methyl ester

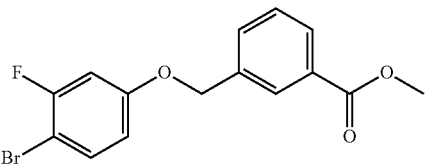

A mixture of 4-bromo-3-fluorophenol (18.34 g, 96 mmol), 3-bromomethylbenzoic acid methyl ester (20 g, 87.3 mmol), potassium carbonate (13.3 g, 96 mmol), and acetone (300 mL) was heated to reflux overnight, followed by cooling to room temperature and filtered. The filtrate was evaporated. The solid was washed with water and cold MeOH to give 3-(4-bromo-3-fluoro-phenoxymethyl)-benzoic acid methyl ester, 28 g (72%). LC-MS (ES) calculated for C15H12BrFO3, 338; obsd 339 [M+H]$^+$.

3-(2,4',5'-Trifluoro-2'-methoxy-biphenyl-4-yloxymethyl)-benzoic acid

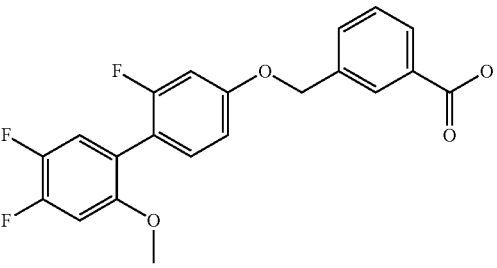

A mixture of 4,5-difluoro-2-methoxyphenylboronic acid (4 g, 21.2 mmol), 3-(4-bromo-3-fluoro-phenoxymethyl)-benzoic acid methyl ester (6 g, 17.7 mmol), CsF (7.3 g, 53 mmol), Pd$_2$(dba)$_3$ (469 mg, 0.51 mmol), Q-Phos (724 mg, 1.02 mmol), and THF (15 mL) was degassed, flashed with nitrogen, and heated at 150° C. in microwave reactor for 20 min. The mixture was then diluted with EtOAc and water, stirred with charcoal, and filtered through celite. The organic layer was separated, washed with water and brine, dried over sodium sulfate, filtered, and evaporated to afford the ester intermediate. The ester was then treated with excess lithium hydroxide in dioxane and water at room temperature overnight to afford 3-(2,4',5'-trifluoro-2'-methoxy-biphenyl-4-yloxymethyl)-benzoic acid (5 g, 84%) upon acidification with dilute HCl. LC-MS (ES) calculated for C21H15F3O4, 338; found m/z 339 [M+H]+.

3-(4-Bromo-2-fluoro-phenoxymethyl)-benzoic acid methyl ester

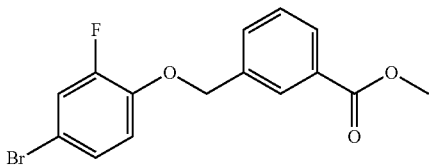

A mixture of 4-bromo-2-fluorophenol (10 g, 52.36 mmol), 3-bromomethylbenzoic acid methyl ester (10.9 g, 47.6 mmol), potassium carbonate (9.9 g, 71.4 mmol), and DMF (100 mL) was stirred at room temperature over the weekend, followed by treatment with water. The precipitate was collected by filtration and washed with water and cold MeOH to give 3-(4-bromo-2-fluoro-phenoxymethyl)-benzoic acid methyl ester. LC-MS (ES) calculated for C15H12BrFO3, 338; found m/z 338 [M+H]+.

3-(4-Bromo-2-fluoro-phenoxymethyl)-benzoic acid

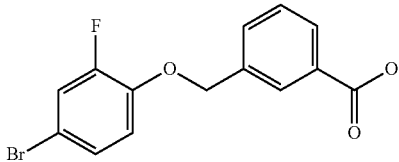

A solution of 3-(4-bromo-2-fluoro-phenoxymethyl)-benzoic acid methyl ester (5.5 g, 16.22 mmol) in dioxane was treated with a solution of lithium hydroxide (1.86 g, 81.1 mmol) in water at room temperature overnight, followed by acidification with concentrated HCl and diluted with water. The precipitate was collected by filtration, washed with water, and dried to give 3-(4-bromo-2-fluoro-phenoxymethyl)-benzoic acid, 5.2 g (99%). LC-MS (ES) calculated for C14H10BrFO3, 323; found m/z 324 [M+H]+.

{{[3-(4-Bromo-2-fluoro-phenoxymethyl)-benzoyl]-methyl-amino}-acetic acid ethyl ester

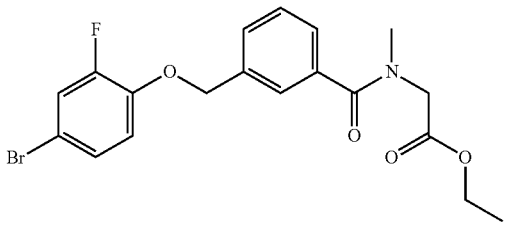

A solution of 3-(4-bromo-2-fluoro-phenoxymethyl)-benzoic acid (5.21 g, 16.02 mmol), N-methyl glycine ethyl ester hydrochloride (4.9 g, 32.05 mmol), DIEA (14 mL, 80.01 mmol), EDCI (6.1 g, 32.05 mmol) and HOAT (4.4 g, 32.05 mmol) in methylene chloride (300 mL) was stirred at room temperature for 12 h. The mixture was evaporated and the residue was purified by column (0-50% EtOAc in hexane) to give {{[3-(4-bromo-2-fluoro-phenoxymethyl)-benzoyl]-methyl-amino}-acetic acid ethyl ester, 4.5 g (66%). LC-MS (ES) calculated for C19H19BrFNO4, 423; found m/z 424 [M+H]+.

Part II: Preparation of Preferred Embodiments of the Invention

Example 1

(S)-1-[3-(2',4'-Difluoro-biphenyl-4-yloxymethyl)-benzoyl]-pyrrolidine-2-carboxylic acid

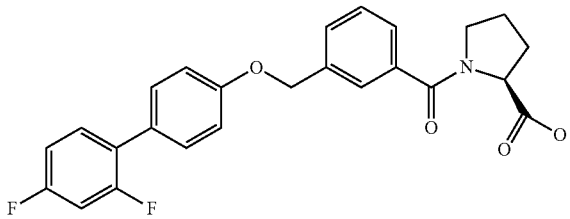

3-(2',4'-Difluoro-biphenyl-4-yloxymethyl)-benzoic acid (4.0 g, 11.76 mmol) in 125 mL toluene was treated with thionyl chloride (8.28 mL, 117.6 mmol) and DMF (200 uL) was heated to 80-90° C. for 3 hrs. The reaction mixture was cooled, evaporated and re-evaporated from toluene 4 times to give a yellow oil that crystallized by pumping under high vacuum. This acid chloride was dissolved in 160 mL acetonitrile to which was added a solution of L-proline (2.62 g, 22.8 mmol) in 33 mL H2O and 1N Na2CO3 (22.8 mL, 22.8 mmol). The reaction mixture was stirred at RT for 45 min, diluted with 300 mL H2O and 450 mL ethyl acetate. The mixture was acidified to pH 2 with 1N HCl. The ethyl acetate layer was separated, washed with H2O, dried over MgSO4 and concentrated in vacuo. The crude product was purified by flash chromatography with a 0-90% gradient of ethyl acetate/MeOH/AcOH (95:5:1) in hexanes to yield 4.67 g (90.8%) of (S)-1-[3-(2',4'-difluoro-biphenyl-4-yloxymethyl)-benzoyl]-pyrrolidine-2-carboxylic acid as a white solid. LC-MS (ES) calculated for C25H21F2NO4, 437.45; found m/z 438.1 [M+H]+.

Example 2

(S)-1-[3-(4',5'-Difluoro-2'-methoxy-biphenyl-4-yloxymethyl)-benzoyl]-pyrrolidine-2-carboxylic acid

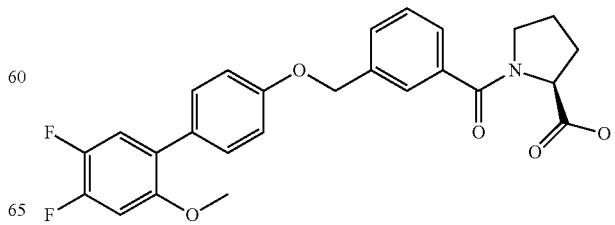

3-(4',5'-Difluoro-2'-methoxy-biphenyl-4-yloxymethyl)-benzoic acid (1.25 g, 3.378 mmol), thionyl chloride (1.227 mL, 16.89 mmol) and DMF (30 uL) in 30 mL toluene were reacted as above to give the acid chloride as a white solid. The acid chloride, L-proline (641 mg, 6.75 mmol) in 8.5 mL $H_2O$ and 1N $Na_2CO_3$ (6.75 mL, 6.75 mmol) were reacted as above and purified by flash chromatography with a 0-50% gradient of ethyl acetate/MeOH/AcOH (95:5:1) in $CH_2Cl_2$ to yield 1.4 g (88.7%) of (S)-1-[3-(4',5'-difluoro-2'-methoxy-biphenyl-4-yloxymethyl)-benzoyl]-pyrrolidine-2-carboxylic acid as a white solid (20 mg, 21%). LC-MS (ES) calculated for C26H23F2NO3, 467.47; found m/z 468.0 [M+H]+.

Example 3

(S)-1-[3-(4',5'-Difluoro-2'-methyl-biphenyl-4-yloxymethyl)-benzoyl]-pyrrolidine-2-carboxylic acid

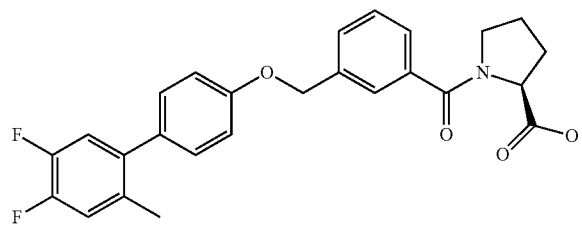

3-(4',5'-Difluoro-2'-methyl-biphenyl-4-yloxymethyl)-benzoic acid (1.1 g, 3.1 mmol), thionyl chloride (1.128 mL, 15.53 mmol) and DMF (100 uL) in 30 mL toluene were reacted as above to give the acid chloride as a white solid. The acid chloride, L-proline (589 mg, 6.2 mmol) in 8.5 mL $H_2O$ and 1N $Na_2CO_3$ (6.2 mL, 6.2 mmol) were reacted as above and purified by flash chromatography with a 0-50% gradient of ethyl acetate/MeOH/AcOH (95:5:1) in $CH_2Cl_2$ to yield 1.2 g (85.8%) of (S)-1-[3-(4',5'-difluoro-2'-methyl-biphenyl-4-yloxymethyl)-benzoyl]-pyrrolidine-2-carboxylic acid as a white solid. LC-MS (ES) calculated for C26H23F2NO4, 451.47; found m/z 452.1 [M+H]+.

Example 4

{[3-(4',5'-Difluoro-2'-methyl-biphenyl-4-yloxymethyl)-benzoyl]-methyl-amino}-acetic acid

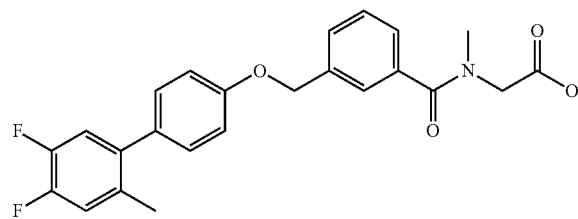

3-(4',5'-Difluoro-2'-methyl-biphenyl-4-yloxymethyl)-benzoic acid (2.2 g, 6.21 mmol), thionyl chloride (1.128 mL, 15.53 mmol) and DMF (100 uL) in 60 mL toluene were reacted as above to give the acid chloride as a white solid. The acid chloride, sarcosine (1.1 g, 12.42 mmol) in 25 mL $H_2O$ and 1N $Na_2CO_3$ (12.42 mL, 12.42 mmol) were reacted as above and purified by flash chromatography with a 0-60% gradient of ethyl acetate/MeOH/AcOH (95:5:1) in $CH_2Cl_2$ to yield 2.5 g (94.6%) of {[3-(4',5'-difluoro-2'-methyl-biphenyl-4-yloxymethyl)-benzoyl]-methyl-amino}-acetic acid as a white solid. LC-MS (ES) calculated for C24H21F2NO4, 425.44; found m/z 426.1 [M+H]+.

Example 5

N-(2-Methanesulfonylamino-2-oxo-ethyl)-N-methyl-3-(2',4',5'-trifluoro-biphenyl-4-yloxymethyl)-benzamide

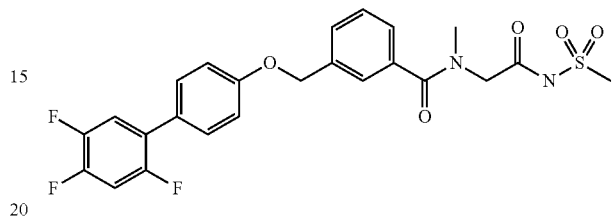

3-(2',4',5'-Trifluoro-biphenyl-4-yloxymethyl)-benzoic acid (1.1 g, 3.07 mmol), thionyl chloride (1.11 mL, 15.36 mmol) and DMF (100 uL) in 30 mL toluene were reacted as above to give the acid chloride as a white solid. The acid chloride, sarcosine (546 mg, 6.14 mmol) in 8.5 mL $H_2O$ and 1N $Na_2CO_3$ (6.14 mL, 6.14 mmol) were reacted as above to yield 1.1 g of {[3-(2',4',5'-trifluoro-biphenyl-4-yloxymethyl)-benzoyl]-methyl-amino}-acetic acid as a white solid. LC-MS (ES) calculated for C23H18F3NO4, 429.40; found m/z 430.1 [M+H]+.

1,1-Carbonyldiimidazole (671 mg, 4.14 mmol) was added to a stirred solution of {[3-(2',4',5'-trifluoro-biphenyl-4-yloxymethyl)-benzoyl]-methyl-amino}-acetic acid (1.1 g, 3.07 mmol) in 5 mL NMP in an ice bath under argon for 3 hrs. To this mixture was added methanesulfonamide (437 mg, 4.6 mmol) and 1,8-diazobicyclo[5.4.0]undec-7-ene (0.684 mL, 4.6 mmol). The reaction was stirred at RT overnight. An additional 0.5 equiv. each of 1,1-carbonyldiimidazole (335 mg, 2.07 mmol), methanesulfonamide (197 mg, 2.07 mmol) and 1,8-diazobicyclo[5.4.0]undec-7-ene (0.34 mL, 2.07 mmol) were added and let stir over the weekend. The reaction mixture was concentrated, dissolved in 250 mL ethyl acetate, washed with H2O and concentrated. The crude product was purified by flash chromatography with a 0-25% gradient of ethyl acetate/MeOH/AcOH (95:5:1) in $CH_2Cl_2$ and lyophilized to yield 153 mg (38.6%) of N-(2-methanesulfonylamino-2-oxo-ethyl)-N-methyl-3-(2',4',5'-trifluoro-biphenyl-4-yloxymethyl)-benzamide as an amorphous solid. LC-MS (ES) calculated for C24H21F2NO5S, 506.50; found m/z 507 [M+H]+.

Example 6

[(S)-2-(1H-Tetrazol-5-yl)-pyrrolidin-1-yl]-[3-(2',4',5'-trifluoro-biphenyl-4-yloxymethyl)-phenyl]-methanone

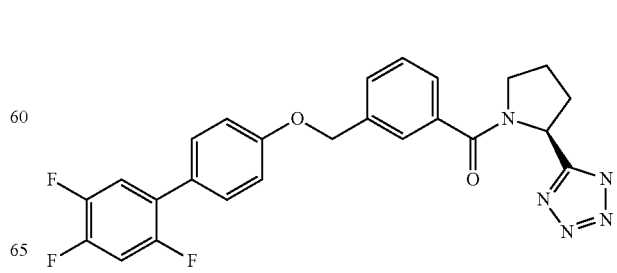

3-(2',4',5'-Trifluoro-biphenyl-4-yloxymethyl)-benzoic acid (1.1 g, 3.07 mmol), thionyl chloride (1.11 mL, 15.36 mmol) and DMF (60 uL) in 30 mL toluene were reacted as above to give the acid chloride as a white solid. The acid chloride, (S)-pyrrolidine-2-carbonitrile (450 mg, 3.37 mmol) and triethylamine (1.3 mL, 9.21 mmol) in 20 mL acetonitrile and 10 mL NMP were stirred at RT overnight. The reaction mixture was diluted with ethyl acetate, washed with sequentially with H$_2$O thoroughly, 1N HCl, and H$_2$O dried over MgSO$_4$ and concentrated in vacuo to give 1.56 g (96.6%) of (S)-1-[3-(2',4',5'-trifluoro-biphenyl-4-yloxymethyl)-benzoyl]-pyrrolidine-2-carbonitrile as a solid. LC-MS (ES) calculated for C25H19F3N2O2, 436.44; found m/z 437 [M+H]$^+$.

(S)-1-[3-(2',4',5'-Trifluoro-biphenyl-4-yloxymethyl)-benzoyl]-pyrrolidine-2-carbonitrile (1.56 g, 3.47 mmol), sodium azide (678 mg, 10.43 mmol) and triethylammonium hydrochloride (1.43 g, 10.43 mmol) in toluene were heated at 100° C. for 17 hrs. The reaction mixture was cooled, concentrated and distributed between 20 mL 0.5N HCl and 100 mL ethyl acetate. The ethyl acetate layer was separated, washed with saturated NaCl, dried over MgSO$_4$, filtered and concentrated. The crude product was purified by flash chromatography with a 0-40% gradient of ethyl acetate/MeOH/AcOH (95:5:1) in CH$_2$Cl$_2$ to give 1.35 g (81.2%) of [(S)-2-(1H-tetrazol-5-yl)-pyrrolidin-1-yl]-[3-(2',4',5'-trifluoro-biphenyl-4-yloxymethyl)-phenyl]-methanone as a white solid. LC-MS (ES) calculated for C25H20F3N5O2, 479.47; found m/z 480.1 [M+H]$^+$.

Example 7

{[3-(4',5'-Difluoro-2'-methoxy-biphenyl-4-yloxymethyl)-benzoyl]-methyl-amino}-acetic acid

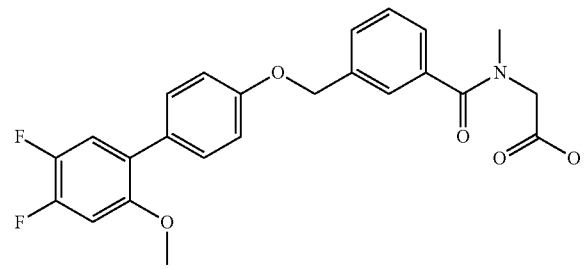

A solution of 3-(4',5'-difluoro-2'-methoxy-biphenyl-4-yloxymethyl)-benzoic acid (20 g, 54 mmol), DIEA (38 mL, 216 mmol), EDCI (15.47 g, 81 mmol) and HOAT (11 g, 81 mmol) in methylene chloride (800 mL) was stirred at room temperature for 1 h, followed by addition of N-methyl glycine ethyl ester hydrochloride (12.44 g, 81 mmol). The resulting mixture was stirred at room temperature for 24 h, then treated with EtOAc (1.5 L) and water (1.5 L). The organic layer was separated, washed with water and brine, dried over sodium sulfate, filtered and evaporated. The oily residue was purified by column (0-35% EtOAc in hexane) to give {[3-(4',5'-difluoro-2'-methoxy-biphenyl-4-yloxymethyl)-benzoyl]-methyl-amino}-acetic acid ethyl ester, 17 g (67%). LC-MS (ES) calculated for C26H25F2NO5, 469; found m/z 470 [M+H]$^+$.

A solution of {[3-(4',5'-difluoro-2'-methoxy-biphenyl-4-yloxymethyl)-benzoyl]-methyl-amino}-acetic acid ethyl ester (17 g, 36 mmol) in dioxane (400 mL) was treated with a solution of LiOH (4.4 g, 180 mmol) in water (400 mL) at room temperature for 12 h, followed by acidification with dilute HCl to pH-2-4. The mixture was extracted with ethyl acetate (3 times). The combined layer was washed with water and brine, dried over sodium sulfate, filtered, and evaporated to give {[3-(4',5'-difluoro-2'-methoxy-biphenyl-4-yloxymethyl)-benzoyl]-methyl-amino}-acetic acid as an off-white solid, 13.5 g (85%), after drying in high vacuum at 60° C. for 48 h. LC-MS (ES) calculated for C26H25F2NO5, 441; found m/z 442 [M+H]$^+$.

Example 8

{tert-Butyl-[3-(4',5'-difluoro-2'-methoxy-biphenyl-4-yloxymethyl)-benzoyl]-amino}-acetic acid

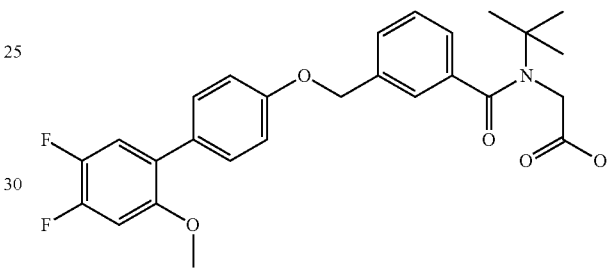

A mixture of 3-(4',5'-difluoro-2'-methoxy-biphenyl-4-yloxymethyl)-benzoic acid (16.44 g, 44.39 mmol), toluene (180 mL), SOCl$_2$ (19.4 mL, 265.8 mmol), and anhydrous DMF (1 mL) was heated to reflux overnight, cooled to room temperature, and evaporated to dryness. The residue was co-evaporated twice with toluene followed by high vacuum at 70° C. for 4 h to give 3-(4',5'-difluoro-2'-methoxy-biphenyl-4-yloxymethyl)-benzoyl chloride as a solid (17 g).

To a solution of 3-(4',5'-difluoro-2'-methoxy-biphenyl-4-yloxymethyl)-benzoyl chloride (10 g, 25.7 mmol), triethylamine (10 mL, 64 mmol) in anhydrous THF (50 mL) was added in portions of tert-butylglycine methyl ester at 0° C., followed by slowly warming up to room temperature overnight while stirring. The mixture was diluted with EtOAc, washed with water and brine, dried over sodium sulfate, filtered and evaporated. The oily residue was purified by column (0-30% EtOAc in hexane) to give {[3-(4',5'-difluoro-2'-methoxy-biphenyl-4-yloxymethyl)-benzoyl]-tert-butyl-amino}-acetic acid ethyl ester, 11.6 g (91%). LC-MS (ES) calculated for C28H29F2NO5, 497; found m/z 498 [M+H]$^+$.

A solution of {[3-(4',5'-difluoro-2'-methoxy-biphenyl-4-yloxymethyl)-benzoyl]-tert-butyl-amino}-acetic acid ethyl ester (11.6 g, 23.3 mmol) in THF (500 mL) was treated with a solution LiOH (2.8 g, 116.7 mmol) in water (500 mL) at room temperature for 12 h. THF was then removed by evaporation. The mixture was then poured into ice and carefully acidified with dilute HCl to pH-1. The precipitate was collected by filtration, washed with water, and dried in vacuum to afford {tert-butyl-[3-(4',5'-difluoro-2'-methoxy-biphenyl-4- yloxymethyl)-benzoyl]-amino}-acetic acid as a white solid, 10.6 g (94%). LC-MS (ES) calculated for C27H27F2NO5, 483; found m/z 484 [M+H]+.

Example 9

{tert-Butyl-[2-(4',5'-difluoro-2'-methoxy-biphenyl-4-yloxymethyl)-thiazole-4-carbonyl]-amino}-acetic acid

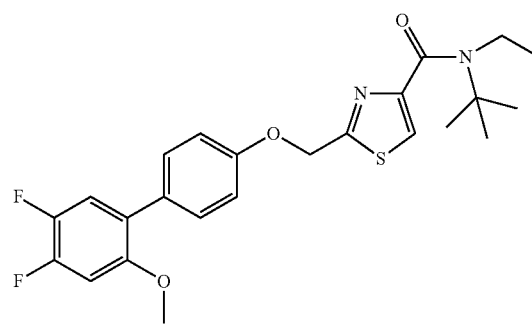

A mixture of 2-(4',5'-difluoro-2'-methoxy-biphenyl-4-yloxymethyl)-thiazole-4-carboxylic acid (22.02 g, 58.35 mmol) in thionyl chloride (70 mL, 959.7 mmol) was heated to reflux and the resulting solution was refluxed for 2½ h. The solution was cooled, concentrated, reconcentrated twice from toluene to give the crude acid chloride. A solution of the crude acid chloride in THF (100 mL) was added over 10 min to a solution of ethyl 2-(tert-butylamino)acetate (10.45 g, 65.63 mmol) and triethylamine (25 mL, 179.4 mmol) in THF (100 mL) stirred in an ice bath at ~0° C. The mixture was allowed to warm to RT and stirred at room temp. for 16 h. The reaction mixture was diluted with ethyl acetate (800 mL), washed with 1/1 water/brine (300 mL), brine (200 mL), dried (MgSO4), filtered, concentrated, flash chromatographed (silica, 350 g, 50% to 100% ethyl acetate in hexanes) and recrystallized from ethyl acetate and hexane to give tert-butyl-[2-(4',5'-difluoro-2'-methoxy-biphenyl-4-yloxymethyl)-thiazole-4-carbonyl]-amino}-acetic acid ethyl ester (19.14 g, 63.3%) as a light tan solid. LC-MS (ES) calculated for $C_{26}H_{28}F_2N_2O_5S$, 518.58; found m/z 519 [M+H]+.

A solution of tert-butyl-[2-(4',5'-difluoro-2'-methoxy-biphenyl-4-yloxymethyl)-thiazole-4-carbonyl]-amino}-acetic acid ethyl ester (19.14 g, 36.91 mmol) in inhibitor free THF (100 mL) was treated with a mixture of lithium hydroxide monohydrate (9.8 g, 233.6 mmol) in water (100 mL) at room temp. The reaction mixture was stirred at RT for 1 h, at 60° C. for 1 h and at 80° C. for 75 min. The reaction mixture was stirred in an ice bath, added aq. 2N HCl and extracted with ethyl acetate (3×300 mL). The organic layers were combined, washed with brine (2×200 mL), dried (MgSO4), filtered, concentrated, triturated with warm ethyl acetate (100 mL) filtered and lypholized from acetonitrile-water to give {tert-butyl-[2-(4',5'-difluoro-2'-methoxy-biphenyl-4-yloxymethyl)-thiazole-4-carbonyl]-amino}-acetic acid (12.47 g, 68.9%) as a white solid. LC-MS calculated for $C_{24}H_{24}F_2N_2O_5S$, 490.53; found m/z 491 [M+H]+.

Example 10

{Methyl-[3-(2',4',5'-trifluoro-biphenyl-4-yloxymethyl)-benzoyl]-amino}-acetic acid

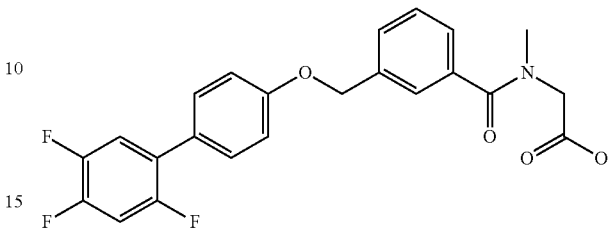

A solution of 3-(2',4',5'-trifluoro-biphenyl-4-yloxymethyl)-benzoic acid (20 g, 56 mmol), N-methyl glycine ethyl ester hydrochloride (12.44 g, 81 mmol), DIEA (29 mL, 167.4 mmol), EDCI (16 g, 84 mmol) and HOAT (12.9 g, 84 mmol) in DMF (100 mL) was stirred at room temperature for 12 h. The mixture was then treated with EtOAc, washed with water and brine, dried over sodium sulfate, filtered and evaporated. The oily residue was purified by column (0-50% EtOAc in hexane) to give the ester intermediate.

A solution of the ester in dioxane (400 mL) was treated with a solution of excess LiOH in water (400 mL) at room temperature for 12 h, followed by pouring into ice and acidification with concentrated HCl while stirring. The stirring was continued at room temperature over the weekend. The white precipitate was collected by filtration, washed with water, air-dried, and finally dried in vacuum at 60° C. to give {methyl-[3-(2',4',5'-trifluoro-biphenyl-4-yloxymethyl)-benzoyl]-amino}-acetic acid as an off-white solid, 20 g (83%). LC-MS (ES) calculated for C23H18F3NO4, 429; found m/z 430 [M+H]+.

Example 11

{Methyl-[3-(2,4',5'-trifluoro-2'-methoxy-biphenyl-4-yloxymethyl)-benzoyl]-amino}-acetic acid

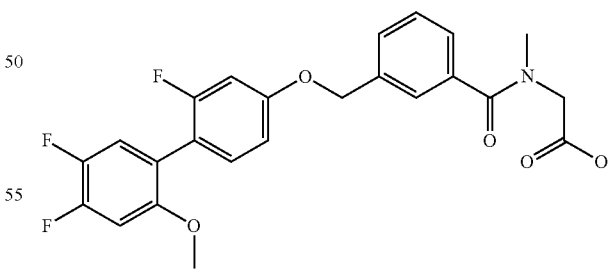

A solution of 3-(2,4',5'-trifluoro-2'-methoxy-biphenyl-4-yloxymethyl)-benzoic acid (2 g, 5.15 mmol), N-methyl glycine ethyl ester hydrochloride (1.2 g, 7.73 mmol), triethylamine (3.6 mL, 25.75 mmol), EDCI (2 g, 10.3 mmol) and HOAT (1.35 g, 10.3 mmol) in methylene chloride (50 mL) was stirred at room temperature for 12 h. The solution was loaded on column and eluted with 0-60% EtOAc in hexane to give the ester intermediate.

A solution of the ester in dioxane was treated with a solution of excess LiOH in water at room temperature for 12 h, followed by acidification with concentrated HCl to give a crude product that was purified by preparative HPLC to afford {methyl-[3-(2,4',5'-trifluoro-2'-methoxy-biphenyl-4-yloxymethyl)-benzoyl]-amino}-acetic acid, 1 g (42%). LC-MS (ES) calculated for C24H20F3NO5, 459; found m/z 460 [M+H]$^+$.

Example 12

Cyclopropanesulfonic acid 3-(2',4',5'-trifluoro-biphenyl-4-yloxymethyl)-benzoylamide

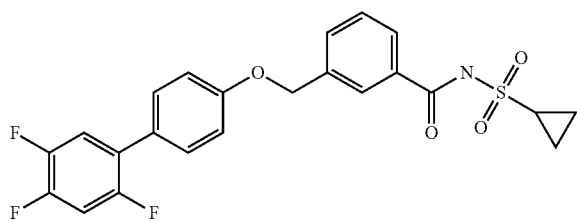

A solution of 3-(2',4',5'-trifluoro-biphenyl-4-yloxymethyl)-benzoic acid methyl ester (18.96 g, 50.92 mmol) in inhibitor free THF (100 mL) was treated with a near solution of lithium hydroxide monohydrate (8.4 g, 200.2 mmol) in water (100 mL) at room temperature and heated at 60° C. for 4 h. The reaction mixture was cooled, diluted with water, acidified with aq. 2N HCl and extracted with ethyl acetate. The organic layers were combined, washed with 1/1 water/brine, brine, dried (MgSO$_4$), filtered and concentrated to give 3-(2',4',5'-trifluoro-biphenyl-4-yloxymethyl)-benzoic acid (17.89 g, 98.0%) as an off white solid. LC-MS (ES) calculated for C$_{20}$H$_{13}$F$_3$O$_3$, 358.32; found m/z 357 [M–H]$^-$.

A solution of 3-(2',4',5'-trifluoro-biphenyl-4-yloxymethyl)-benzoic acid (5.0 g, 13.96 mmol) in THF (100 mL) was treated with CDI (3.37 g, 20.78 mmol), heated at 50° C. for 30 min, cooled to room temperature, added cyclopropanesulfonamide (1.86 g, 15.35 mmol) and DBU (4.2 mL, 28.08 mmol) and heated at 60° C. for 17 h. The reaction mixture was cooled to room temperature, treated with aqueous 2N HCl (50 mL), stirred for 10 min, added water (50 mL) and extracted with ethyl acetate (3×100 mL). The organic layers were combined, washed with conc. HCl (20 mL), water (50 mL), 1/1 water/brine (50 mL), brine (50 mL), dried (MgSO$_4$), filtered, concentrated from methanol to give cyclopropanesulfonic acid 3-(2',4',5'-trifluoro-biphenyl-4-yloxymethyl)-benzoylamide (2.58 g, 40.1%) as a white solid. LC-MS (ES) calculated for C$_{23}$F$_{18}$F$_3$NO$_4$S, 461.46; found m/z 460 [M–H]$^-$.

Example 13

{[3-(4',5'-Difluoro-2'-methoxy-biphenyl-4-yloxymethyl)-4-fluoro-benzoyl]-methyl-amino}-acetic acid

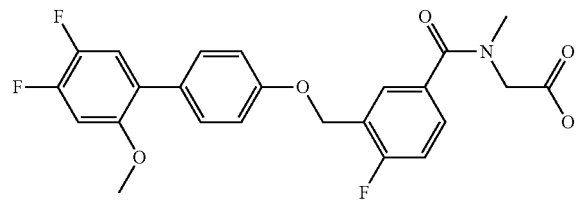

To a mixture of 3-(4',5'-difluoro-2'-methoxybiphenyl-4-yloxymethyl)-4-fluorobenzoic acid (0.3 g, 0.77 mmol) and N-methyl-glycine ethyl ester hydrochloride (0.7 g, 4.5 mmol) in methylene chloride (40 mL) was added HOAT (0.2 g, 1.46 mmol), EDCI (0.3 g, 1.56 mmol) and triethylamine (1.4 mL, 10 mmol). The mixture was stirred at room temperature for 3 hrs and extracted with methylene chloride and dilute hydrochloric acid. The organic layer was dried and concentrated. The residue was purified through flash column chromatography (80 g silica gel, 5% to 60% ethyl acetate in hexanes over 25 minutes) to give amorphous material as {[3-(4',5'-difluoro-2'-methoxy-biphenyl-4-yloxymethyl)-4-fluoro-benzoyl]-methyl-amino}-acetic acid ethyl ester (0.29 g, 77%).

{[3-(4',5'-Difluoro-2'-methoxy-biphenyl-4-yloxymethyl)-4-fluoro-benzoyl]-methyl-amino}-acetic acid ethyl ester (0.29 g, 0.59 mmol) was dissolved in THF (25 mL) and lithium hydroxide solution (0.5N, 2 mL) was added. The mixture was stirred at room temperature for 2 hrs. Solvents were evaporated and the residue was treated with dilute hydrochloric acid and ethyl acetate. The organic layer was washed with brine and dried over sodium sulfate. Solvent was evaporated and the residue was dissolved in acetonitrile (1 mL) and diluted with water (8 mL). The mixture was lyophilized to give a fluffy solid as {[3-(4',5'-difluoro-2'-methoxy-biphenyl-4-yloxymethyl)-4-fluoro-benzoyl]-methyl-amino}-acetic acid (0.26 g, 96%). HRMS (ES) calculated for C$_{24}$H$_{20}$F$_3$NO$_5$, 482.1186; found m/z 482.1185 [M+Na]$^+$; $^1$H-NMR (DMSO-d$_6$) δ ppm 12.86 (br s, 1H), 7.29-7.69 (m, 6H), 7.24 (dd, J=13.0, 7.2 Hz, 1H), 7.08 (d, J=8.5 Hz, 2H), 5.19 and 5.23 (s, 2H, rotamer), 3.97 and 4.14 (s, 2H, rotamer), 3.76 (s, 3H), 2.94 and 2.95 (s, 3H, rotamer).

Example 14

{{Methyl-[3-(3,2',4',5'-tetrafluoro-biphenyl-4-yloxymethyl)-benzoyl]-amino}-acetic acid

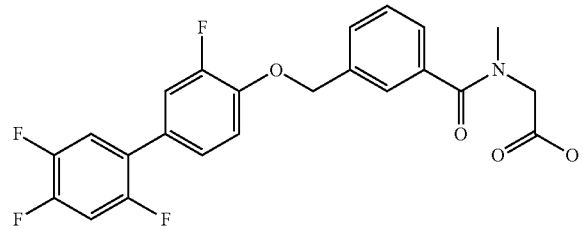

A mixture of {{[3-(4-bromo-2-fluoro-phenoxymethyl)-benzoyl]-methyl-amino}-acetic acid ethyl ester (600 mg, 1.51 mmol), 2,4,5-trifluorophenylboronic acid (400 mg, 2.27 mmol), Pd(dppf)Cl$_2$ methylene chloride complex (37 mg, 0.045 mmol), potassium carbonate (520 mg, 3.8 mmol), DMF (12 mL) and water (3 mL) was degassed, flashed with nitrogen, heated at 150° C. for 60 minutes in microwave reactor. The mixture was acidified by conc. HCl and diluted with water. Solvent was then removed by decantation and the sticky residue was purified by preparative HPLC to afford {{methyl-[3-(3,2',4',5'-tetrafluoro-biphenyl-4-yloxymethyl)-benzoyl]-amino}-acetic acid, 171 mg (25%). LC-MS (ES) calculated for C23H17F4NO4, 447; found m/z 448 [M+H]$^+$.

Example 15

(R)-1-[3-(4',5'-Difluoro-2'-methoxy-biphenyl-4-yloxymethyl)-benzoyl]-pyrrolidine-2-carboxylic acid

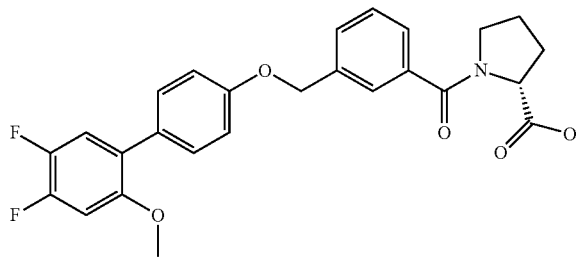

A solution of 3-(4',5'-difluoro-2'-methoxy-biphenyl-4-yloxymethyl)-benzoic acid (25 g, 67.55 mmol), D-proline methyl ester hydrochloride (16.8 g, 101.32 mmol), DIEA (35 mL, 202.65 mmol), EDCI (19.4 g, 101.32 mmol) and HOAT (13.8 g, 101.32 mmol) in DMF (200 mL) was stirred at room temperature for 12. The mixture was then diluted with EtOAc, washed with 10% sodium carbonate, water, and brine, dried over sodium sulfate, filtered and evaporated. The residue was purified by column (0-50% EtOAc in hexane) to afford the ester intermediate.

A solution of the ester in dioxane was treated with a solution of excess LiOH in water at room temperature for 12 h, followed by acidification with concentrated HCl under cooling in ice-water bath. The mixture was extracted with EtOAc. The combined organic layers were washed with water and brine, dried over sodium sulfate, filtered and evaporated. The oily product was co-evaporated three times with acetonitrile, followed by high vacuum evaporation at 50° C. to give (R)-1-[3-(4',5'-difluoro-2'-methoxy-biphenyl-4-yloxymethyl)-benzoyl]-pyrrolidine-2-carboxylic acid as a white solid, 28.9 g (91%). LC-MS (ES) calculated for C26H23F2NO5, 467; found m/z 468 [M+H]$^+$.

Example 16

Glycogen Synthase (GS) Assay

The following tests were carried out in order to determine the activity of the compounds of formula (I).

Twelve μL per well of substrate solution containing glycogen (4.32 mg/ml), 2.67 mM UDP-glucose, 21.6 mM phospho(enol)pyruvate and 2.7 mM NADH in 30 mM glycylglycine, pH 7.3 buffer was added into a polystyrene 384-well assay plate (BD Biosciences).

Compound solutions (8 μL/well) at various concentrations (0-300 μM) were added to the assay plate (columns 5-24). Compound solution contains 30 mM glycylglycine, pH 7.3, 40 mM KCl, 20 mM MgCl$_2$, 9.2% DMSO, with (columns 15-24) or without (columns 5-14) 20 mM glucose 6-phosphate.

Enzyme solution (12 μL/well) containing glycogen synthase (16.88 μg/ml), pyruvate kinase (0.27 mg/ml), lactate dehydrogenase (0.27 mg/ml) in 50 mM Tris-HCl, pH 8.0, 27 mM DTT and bovine serum albumin (BSA, 0.2 mg/ml) was added to the assay plate (columns 3-24). As a blank control, enzyme solution without glycogen synthase was added into the top half wells of columns 1-2. To the bottom half wells of columns 1-2 were added a known activator, glucose 6-phosphate (at final concentration 5 mM) in addition to the enzyme solution. The reaction mixture was incubated at room temperature. The assay plate was then read for absorbance at 340 nm on an Envision reader every 3 minutes up to a total of 15 minutes.

The enzyme activity (with or without compound) was calculated by the reaction rate and represented by the optical density change (δOD) per minute. Percent stimulation of glycogen synthase activity by a compound at various concentrations was calculated by the following formula:

% stimulation=100*Rs/Rt,

Where Rs is the reaction rate of the enzyme in the presence of compound and Rt is the reaction rate of the enzyme in the absence of compound.

$SC_{200}$ is defined as the compound concentration that is needed to stimulate 200% of the enzyme activity. $EC_{50}$ is defined as the compound concentration that is needed to give 50% maximum activation.

The compounds from Examples 1 to 15 were assayed according to assay procedures described above and the results are listed in Table 1 below:

TABLE 1

Glycogen Synthase Activation Potency of Example Compounds

| Example Number | GS $SC_{200}$ (μM) | GS $EC_{50}$ (μM) |
|---|---|---|
| 1 | 0.02 | 0.12 |
| 2 | 0.02 | 0.14 |
| 3 | 0.001 | 0.04 |
| 4 | 0.01 | 0.08 |
| 5 | 0.07 | 0.2 |
| 6 | 0.59 | 2.1 |
| 7 | 0.02 | 0.1 |
| 8 | 0.01 | 0.2 |
| 9 | 0.01 | 0.11 |
| 10 | 0.04 | 0.1 |
| 11 | 0.01 | 0.16 |
| 12 | 0.14 | 0.69 |
| 13 | 0.004 | 0.08 |
| 14 | 0.01 | 0.1 |
| 15 | 0.05 | 0.22 |

It is to be understood that the invention is not limited to the particular embodiments of the invention described above, as variations of the particular embodiments may be made and still fall within the scope of the appended claims.

What is claimed is:

1. A compound, wherein said compound is:
   (S)-1-[3-(2',4'-Difluoro-biphenyl-4-yloxymethyl)-benzoyl]-pyrrolidine-2-carboxylic acid;
   (S)-1-[3-(4',5'-Difluoro-2'-methoxy-biphenyl-4-yloxymethyl)-benzoyl]-pyrrolidine-2-carboxylic acid;
   (S)-1-[3-(4',5'-Difluoro-2'-methyl-biphenyl-4-yloxymethyl)-benzoyl]-pyrrolidine-2-carboxylic acid;
   {[3-(4',5'-Difluoro-2'-methyl-biphenyl-4-yloxymethyl)-benzoyl]-methyl-amino}-acetic acid;
   N-(2-Methanesulfonylamino-2-oxo-ethyl)-N-methyl-3-(2',4',5'-trifluoro-biphenyl-4-yloxymethyl)-benzamide;
   [(S)-2-(1H-Tetrazol-5-yl)-pyrrolidin-1-yl]-[3-(2',4',5'-trifluoro-biphenyl-4-yloxymethyl)-phenyl]-methanone;
   {tert-Butyl-[3-(4',5'-difluoro-2'-methoxy-biphenyl-4-yloxymethyl)-benzoyl]-amino}-acetic acid;
   {tert-Butyl-[2-(4',5'-difluoro-2'-methoxy-biphenyl-4-yloxymethyl)-thiazole-4-carbonyl]-amino}-acetic acid;
   {Methyl-[3-(2',4',5'-trifluoro-biphenyl-4-yloxymethyl)-benzoyl]-amino}-acetic acid;
   {Methyl-[3-(2,4',5'-trifluoro-2'-methoxy-biphenyl-4-yloxymethyl)-benzoyl]-amino}-acetic acid;

Cyclopropanesulfonic acid 3-(2',4',5'-trifluoro-biphenyl-4-yloxymethyl)-benzoylamide;

{[3-(4',5'-Difluoro-2'-methoxy-biphenyl-4-yloxymethyl)-4-fluoro-benzoyl]-methyl-amino}-acetic acid;

{{Methyl-[3-(3,2',4',5'-tetrafluoro-biphenyl-4-yloxymethyl)-benzoyl]-amino}-acetic acid; or (R)-1-[3-(4',5'-Difluoro-2'-methoxy-biphenyl-4-yloxymethyl)-benzoyl]-pyrrolidine-2-carboxylic acid.

2. A pharmaceutical composition, comprising a therapeutically effective amount of a compound according to claim 1 and a pharmaceutically acceptable carrier and/or adjuvant.

* * * * *

UNITED STATES PATENT AND TRADEMARK OFFICE
CERTIFICATE OF CORRECTION

| | | |
|---|---|---|
| PATENT NO. | : 8,039,495 B2 | Page 1 of 1 |
| APPLICATION NO. | : 12/905313 | |
| DATED | : October 18, 2011 | |
| INVENTOR(S) | : David Robert Bolin et al. | |

It is certified that error appears in the above-identified patent and that said Letters Patent is hereby corrected as shown below:

Title page item (73) in Column 1, delete "Hoffman" and insert --Hoffmann--.

Title page item (74) in Column 2, delete "George W. Johnson" and insert --George W. Johnston--.

Signed and Sealed this
Seventeenth Day of April, 2012

David J. Kappos
*Director of the United States Patent and Trademark Office*